United States Patent
Fong et al.

(10) Patent No.: US 6,348,330 B1
(45) Date of Patent: Feb. 19, 2002

(54) METHOD FOR MEASURING HUMAN NEUROKININ-3 RECEPTOR LIGAND BINDING

(75) Inventors: Tung Ming Fong, Somerset; Ruey-Ruey C. Huang, Towaco; Catherine D. Strader, Verona, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/482,971

(22) Filed: Jan. 12, 2000

Related U.S. Application Data

(63) Continuation of application No. 08/090,369, filed on Jul. 12, 1993, now Pat. No. 6,258,943, which is a continuation of application No. 07/851,974, filed on Mar. 16, 1992, now abandoned.

(51) Int. Cl.[7] .......................... C07H 21/04; C07K 2/00; C12N 15/63; C12Q 1/68; G01N 33/53
(52) U.S. Cl. ........................ 435/69.1; 435/7.1; 435/7.2; 435/69.1; 435/320.1; 435/325; 435/358; 436/501; 530/300; 530/350; 536/23.5
(58) Field of Search ........................ 435/4, 6, 7.1, 7.21, 435/69.1, 320.1, 325, 358, 7.2; 436/501, 503, 504; 530/300, 350; 536/23.5

(56) References Cited

U.S. PATENT DOCUMENTS 5,336,595 A * 8/1994 Strader et al. ............. 435/6

FOREIGN PATENT DOCUMENTS

WO    WO 92/16547    10/1993

OTHER PUBLICATIONS

Huang et al. cDNa sequence and heterologous expression of the human neurokinin-3 receptor. Biochem Biophys Res Comm 184(2): 966–972, 1992.*
Buell, et al., "Molecular Characterisation, Expression and Localisation of Human Neurokinin-3 Receptor", *Febs. Lett.*, 299, No. 1, 90–95 (1992).
Cascieri, et al., "Characterization of the Substance P Receptor in Rat Brain Cortex Membranes . . . ", *J. Biol. Chem.*, 258, 5158–5164 (1983).
Fong, et al. (I), "Differential Activation of Intracellular Effector by Two Isoforms of Human Neurokinin–1 Receptor", *Mol. Pharm.*, 41, 24–30 (1992).
Fong, et al. (II), "Molecular Basis for the Species Selectivity of the Neurokinin–1 Receptor Antagonists . . . ", *J. Biol.*, 267(36), 25668–671 (1992).
Gerard, et al. (I), "The Human Neurokinin A (Substance K) Receptor", *J. Biol. Chem.*, 265, 20455–62 (1990).
Gerard, et al. (II), "Molecular Cloning and Chromosomal Lacalization of the Human Substance P Receptor Gene", *FASEB J.*, 5(5), 4647 (1991).
Gerard, et al. (III), "Human Substance P Receptor (NK–1): Organization of the Gene, Chromosome . . . ", *Biochem.*, 30(44), 10640–46 (1991).
Guan, et al., "Identification of a Single Amino Acid Residue Responsible for the Binding of a Class of Beta–Adrenergic . . . ", *Mol. Pharm.*, 41, 695–698 (1992).
Hershey, et al., "Molecular Characterization of a Functional cDNA Encoding the Rat Substance P Receptor", *Science*, 247, 958–962 (1990).
Hopkins, et al., "Isolation and Characterization of the Human Lung NK–1 Receptor cDNA", *Biochem. Biophys. Res. Commun.*, 180, 1110–1117 (1991).
Kobilka, et al., "cDNA for the Human 2–Adrenergic Receptor: A Protein with Multiple Membrane . . . ", *Proc. Natl. Acad. Sci.*, USA, 84, 46–50 (1987).
Laneuville, et al., "Characterization of the Effects Produced by Neurokinins and Three Agonists Selective for Neurokinin . . . ", *Life Sci.*, 42, 1295–1305 (1988).
Lundblad, et al., "Origin and Distribution of Capsaicin, Sensitive Substance P–Immunoreactive . . . ", *Acta Otolarynygol*, 96, 485–493 (1983).
Masu, et al., "cDNA Cloning of Bovine Substance–K Receptor Through Oocyte Expression System", *Nature*, 329, 836–838 (1987).
McLean, et al., "Activity and Distribution of Binding Sites in Brain of a Nonpeptide Substance P (NK1) Receptor Antagonist", *Science*, 251, 437–439 (1991).
Oksenberg, et al., "A Single Amino–Acid Difference Confers Major Pharmacological Variation Betwen Human and Rodent 5–HT1B Receptors", *Nature*, 360, 161–163 (1992).
Payan, et al., "Specific Stimulation of Human T Lymphocytes by Substance P", *J. Immunol.*, 131, 1613–15 (1983).
Sachais, et al., "Molecular Basis for the Species Selectivity of the Substance P Antagonist CP–963,345", *J. Biol. Chem.*, 268 (4), 2319–23 (1993).
Sasai, et al., "Molecular Characterization of Rat Substance K Receptor and Its mRNAs", *Biochem. Biophys. Res. Commun.*, 165, 695–702 (1989).
Shigemoto, et al., "Cloning and Expression of Rat Neuromedin K Receptor cDNA", *J. Biol. Chem.*, 265, 623—628 (1990).

(List continued on next page.)

*Primary Examiner*—Elizabeth Kemmerer
*Assistant Examiner*—Bridget E. Bunner
(74) *Attorney, Agent, or Firm*—J. Eric Thies; David L. Rose

(57) ABSTRACT

A recombinant human neurokinin-3 receptor (hereinafter identified as human NK3R) is disclosed which has been prepared by polymerase chain reaction techniques. Also disclosed is the complete sequence of human NK3R complementary DNA; expression systems, including a CHO (chinese hamster ovarian cell line) stable expression system; and an assay using the CHO expression system. Human NK3R can be used in an assay to identify and evaluate entities that bind to the neurokinin-3 receptor.

4 Claims, No Drawings

OTHER PUBLICATIONS

Shigetada, "Substance P Receptor and Gene Thereof", *Patent Abstracts of Japan*, 015(341), 29 Aug. 91, (JP3133998).

Suryanarayana, et al., "A Point Mutation in the Seventh Hydrophobic Domain of the a2 Adrenergic Receptor . . . ", *J. Biol. Chem.*, 266 (23), 15488–15492 (1991).

Takeda, et al., "Molecular Cloning, Structural Characterization & Functional Expression of the Human Substance P Receptor", *Biochem. & Biophys. Res. Comm.*, 179(3), 1232–40 (1991).

Yokata, et al., "Molecular Charaterization of a Functional cDNA for Rat Substance P Receptor", *J. Biol. Chem.*, 264, (30) 17649–52 (1989).

Hershey, et al., "Molecular and Genetic Characterization, Functional Expression, and mRNA Expression . . . ", *Ann .of the N.Y. Acad. of Sciences*, vol. 632, pp. 63–78 (1991).

Ohkubo, et al., "Molecular Characterization of the Three Tachykinin Receptors", *Ann.of the N.Y. Acad. of Sciences*, vol. 632, pp. 53–62 (1991).

Regali, et al., "Receptors for Substance P and Related Neurokinins", *Pharmacology*, vol. 38(1), pp. 1–15 (1989).

Tschida, "Tissue Distribution and Quantitation of the mRNAs for Three Rat Tachykinin Receptors", *Eur. Jour. Biochem.*, vol. 193, pp. 751–757 (1990).

Dietl, et al., "Phylogeny of tachykinin receptor localization . . . " *Brain Res.*, 539, 211–222 (1991).

Shook et al. A novel Bioassay for the NK–2 neurokinin receptor: the guinea pig gallbladder. Life Sciences 39: 2533–2539, 1986.*

Cascieri et al. Determination of the amino acid residues in substance P conferring selectivity and specificity for the rat neurokinin receptors. Molec Pharmacol 41(6): 1096–1099, 1992.*

Takahashi et al. The primary structure and gene organization of human substance P and neuomedin K receptors. Eur J Biochem 204: 1025–1033, 1992.*

Hunter et al. Pharmacological analysis of 125I–Bolton and Hunter labelled eledoisin binding sites in rat spinal cord by quantitative autoradiography. Neurosci Letters 78(1): 12–16, 1987.*

Beresford et al. Ontogeny and characterization of 125I–Bolton Hunter–eledoisin binding sites in rat spinal cord by quantitative autoradiography. Neurosci 46(1): 225–232, 1992.*

Lavielle et al. Selective agonists of tachykinin binding sites. Fundam Clin Pharmacol 4: 257–268, 1990.*

* cited by examiner

METHOD FOR MEASURING HUMAN NEUROKININ-3 RECEPTOR LIGAND BINDING

This application is a continuation of U.S. application Ser. No. 08/090,369, filed Jul. 12, 1993, now U.S. Pat. No. 6,258,943, which is a continuation of U.S. application Ser. No. 07/851,974, filed Mar. 16, 1992, now abandoned.

BACKGROUND OF THE INVENTION

The present invention concerns a cloned human neurokinin-3 receptor (hereinafter identified as human NK3R).

Neurokinin B (NKB) is a naturally occuring peptide belonging to the neurokinin family of peptides, which also includes substance P (SP) and substance K (SK). NKB binds preferentially to the neurokinin-3 receptor (NK3R), although it also recognizes the other two receptor subtypes (NK1 and NK2) with lower affinity. As is well known in the art, neurokinin B and other tachykinins have been implicated in the pathophysiology of numerous diseases. Neurokinin peptides are reportedly involved in nociception and neurogenic inflammation. The physiological function of NK3R has been implicated in the regulation of enkephalin release, while the NK1 and NK2 receptor subtypes are involved in synaptic transmission (Laneuville et al., *Life Sci.*, 42:1295–1305 (1988)). Since the NKB genomic structure and subcellular distribution are different from those of SP and SK, the physiological function and regulatory mechanism of NKB may be different from SP and SK.

More specifically, neurokinin B is a pharmacologically-active neuropeptide that is produced in mammals and possesses a characteristic amino acid sequence that is illustrated below:

Asp-Met-His-Asp-Phe-Phe-Val-Gly-Leu-Met-NH2.

Several groups have reported the cloning of certain neurokinin receptors. T. M. Fong, et al., *Mol. Pharmacol.*, 41:24–30 (1991) have reported cloned human neurokinin-1 and neurokinin-1 short form receptor. J. Yokota, et al., *J. Biol. Chem.*, 264:17649 (1989) have reported cloned rat neurokinin-1 receptor. N. P. Gerard, et al., *J. Biol. Chem.*, 265:20455 (1990), have reported human neurokinin-2 receptor. Cloned rat and bovine neurokinin-2 receptor have likewise been reported. See respectively, Y. Sasi, and S. Nakanishi, *Biochem Biophys. Res. Comm.*, 165:695 (1989), and Y. Masu, et al., *Nature* 329:836 (1987). Cloned rat neurokinin-3 receptor has been reported by R. Shigemoto, et al., *J. Biol. Chem.*, 265:623 (1990). The above references, however, neither disclose nor suggest the present invention.

The instant invention also concerns an assay protocol which can be used to determine the activity in body fluids of substances that bind human NK3R; these include neurokinin B. The assay can also be used for identifying and evaluating substances that bind NK3R. Thus, the assay can be used to identify neurokinin B antagonists and evaluate their binding affinity. Another method for an assay includes that described by M. A. Cascieri, et al., *J. Biol. Chem.*, 258:5158 (1983). See also, for example, R. M. Snider, et al., *Science*, 251:435 (1991) and S. McLean, et al., *Science*, 251:437 (1991). See also WIPO Patent Publications WO90/05525 and WO90/05729, published May 31, 1990. Methods to date have proven inferior, in part, for failure of the animal receptor (animal NK1R, NK2R or NK3R) activity to accurately reflect that of the human neurokinin-3 receptor. Furthermore, prior to this disclosure, human NK3R has not been available in a highly purified form or in substantial isolation from NK1R and/or NK2R. Use of such neurokinin receptor sources can not accurately depict the affinity of an agonist or an antagonist for a human NK3R.

SUMMARY OF THE INVENTION

A novel recombinant human neurokinin-3 receptor (hereinafter identified as human NK3R) is disclosed which has been prepared by polymerase chain reaction techniques. Also disclosed is the complete sequence of human NK3R complementary DNA; expression systems, including a CHO (chinese hamster ovarian cell line) stable expression system; and an assay using the CHO expression system.

Human NK3R can be used in an assay to identify and evaluate entities that bind neurokinin B receptor or NK3R. The assay can also be used in conjunction with diagnosis and therapy to determine the body fluid concentration of neurokinin-B related substances in patients. In addition, the complete sequence of the human NK3R is useful in the process of developing novel NK3 agonists and antagonists by computer modeling.

DETAILED DESCRIPTION OF THE INVENTION

One embodiment of the invention concerns human neurokinin-3 receptor, said receptor being free of other human receptor proteins.

In one class this first embodiment concerns human neurokinin-3 receptor, said receptor being free of other human proteins.

Within this class, this first embodiment concerns human neurokinin-3 receptor from human cells such as glioblastoma, said receptor being free of other human proteins.

Also within this class, this first embodiment concerns human neurokinin-3 receptor, the receptor being recombinantly produced from non-human cells.

In a second class, this first embodiment concerns a protein corresponding to the amino acid sequence of human neurokinin-3 receptor, the protein comprising 465 amino acids. Within the second class this first embodiment concerns a protein comprising the following 465 amino acid sequence (SEQ ID NO:1:) depicted from the amino to the carboxy terminus:

```
Met Ala Thr Leu Pro Ala Ala Glu Thr Trp Ile Asp Gly Gly Gly
1               5                   10                  15

Val Gly Ala Asp Ala Val Asn Leu Thr Ala Ser Leu Ala Ala Gly Ala
            20                  25                  30

Ala Thr Gly Ala Val Glu Thr Gly Trp Leu Gln Leu Leu Asp Gln Ala
        35                  40                  45

Gly Asn Leu Ser Ser Ser Pro Ser Ala Leu Gly Leu Pro Val Ala Ser
    50                  55                  60
```

-continued

```
Pro Ala Pro Ser Gln Pro Trp Ala Asn Leu Thr Asn Gln Phe Val Gln
65              70                  75                  80

Pro Ser Trp Arg Ile Ala Leu Trp Ser Leu Ala Tyr Gly Val Val Val
                85                  90                  95

Ala Val Ala Val Leu Gly Asn Leu Ile Val Ile Trp Ile Ile Leu Ala
                100                 105                 110

His Lys Arg Met Arg Thr Val Thr Asn Tyr Phe Leu Val Asn Leu Ala
                115                 120                 125

Phe Ser Asp Ala Ser Met Ala Ala Phe Asn Thr Leu Val Asn Phe Ile
        130                 135                 140

Tyr Ala Leu His Ser Glu Trp Tyr Phe Gly Ala Asn Tyr Cys Arg Phe
145                 150                 155                 160

Gln Asn Phe Phe Pro Ile Thr Ala Val Phe Ala Ser Ile Tyr Ser Met
                165                 170                 175

Thr Ala Ile Ala Val Asp Arg Tyr Met Ala Ile Ile Asp Pro Leu Lys
                180                 185                 190

Pro Arg Leu Ser Ala Thr Ala Thr Lys Ile Val Ile Gly Ser Ile Trp
        195                 200                 205

Ile Leu Ala Phe Leu Leu Ala Phe Pro Gln Cys Leu Tyr Ser Lys Thr
    210                 215                 220

Lys Val Met Pro Gly Arg Thr Leu Cys Phe Val Gln Trp Pro Glu Gly
225                 230                 235                 240

Pro Lys Gln His Phe Thr Tyr His Ile Ile Val Ile Ile Leu Val Tyr
                245                 250                 255

Cys Phe Pro Leu Leu Ile met Gly Ile Thr Tyr Thr Ile Val Gly Ile
                260                 265                 270

Thr Leu Trp Gly Gly Glu Ile Pro Gly Asp Thr Cys Asp Lys Tyr His
        275                 280                 285

Glu Gln Leu Lys Ala Lys Arg Lys Val Val Lys Met Met Ile Ile Val
    290                 295                 300

Val Met Thr Phe Ala Ile Cys Trp Leu Pro Tyr His Ile Tyr Phe Ile
305                 310                 315                 320

Leu Thr Ala Ile Tyr Gln Gln Leu Asn Arg Trp Lys Tyr Ile Gln Gln
                325                 330                 335

Val Tyr Leu Ala Ser Phe Trp Leu Ala Met Ser Ser Thr Met Tyr Asn
                340                 345                 350

Pro Ile Ile Tyr Cys Cys Leu Asn Lys Arg Phe Arg Ala Gly Phe Lys
                355                 360                 365

Arg Ala Phe Arg Trp Cys Pro Phe Ile Lys Val Ser Ser Tyr Asp Glu
        370                 375                 380

Leu Glu Leu Lys Thr Thr Arg Phe His Pro Asn Arg Gln Ser Ser Met
385                 390                 395                 400

Tyr Thr Val Thr Arg Met Glu Ser Met Thr Val Val Phe Asp Pro Asn
                405                 410                 415

Asp Ala Asp Thr Thr Arg Ser Ser Arg Lys Lys Arg Ala Thr Pro Arg
                420                 425                 430

Asp Pro Ser Phe Asn Gly Cys Ser Arg Arg Asn Ser Lys Ser Ala Ser
        435                 440                 445

Ala Thr Ser Ser Phe Ile Ser Ser Pro Tyr Thr Ser Val Asp Glu Tyr
    450                 455                 460

Ser
465.
```

Within the second class this first embodiment also concerns a protein comprising the foregoing amino acid sequence (SEQ ID:NO:1:), the protein being free of other human receptor proteins.

A second embodiment concerns a DNA sequence encoding the human neurokinin-3 receptor, the DNA sequence being free of other human DNA sequences.

As will be appreciated by those of skill in the art, there is a substantial amount of redundancy in the set of codons which translate specific amino acids. Accordingly, the invention also includes alternative base sequences wherein a codon (or codons) are replaced with another codon, such that the amino acid sequence translated by the DNA sequence remains unchanged. For purposes of this specification, a sequence bearing one or more such replaced codons will be defined as a degenerate variation. Also included are mutations (exchange of individual amino acids) which one of skill in the art would expect to have no effect on functionality, such as valine for leucine, arginine for lysine and asparagine for glutamine.

One class of the second embodiment of the invention concerns the following nucleotide sequence (SEQ ID NO:2:) of complementary DNA depicted from the 5' to the 3' terminus:

```
CTATTGCAGT ATCTTTCAGC TTCCAGTCTT ATCTGAAGAC CCCGGCACCA AAGTGACCAG      60
GACGGAGAGA AGAACTTCAG AGGAGTCTCG TCTTGGGCTG CCCGTGGGTG AGTGGGAGGG     120
TCCGGCAGTG CAGACCGGTG GCGATGGCCA CTCTCCCAGC AGCAGAAACC TGGATAGACG     180
GGGGTGGAGG CGTGGGTGCA GACGCCGTGA ACCTGACCGC CTCGCTAGCT GCCGGGGCGG     240
CCACGGGGGC AGTTGAGACT GGGTGGCTGC AACTGCTGGA CCAAGCTGGC AACCTCTCCT     300
CCTCCCCTTC CGCGCTGGGA CTGCCTGTGG CTTCCCCCGC GCCCTCCCAG CCCTGGGCCA     360
ACCTCACCAA CCAGTTCGTG CAGCCGTCCT CGCGCATCCC GCTCTGGTCC CTGGCGTATG     420
GTGTGGTGGT GGCAGTGGCA GTTTTGGGAA ATCTCATCGT CATCTGGATC ATCCTGGCCC     480
ACAAGCGCAT GAGGACTGTC ACCAACTACT TCCTTGTGAA CCTGGCTTTC TCCGACGCCT     540
CCATGGCCGC CTTCAACACG TTGGTCAATT TCATCTACGC GCTTCATAGC GAGTGGTACT     600
TTGGCGCCAA CTACTGCCGC TTCCAGAACT TCTTTCCTAT CACAGCTGTG TTCGCCAGCA     660
TCTACTCCAT GACGGCCATT GCGGTGGACA GGTATATGGC TATTATTGAT CCCTTGAAAC     720
CCAGACTGTC TGCTACAGCA ACCAAGATTG TCATTGGAAG TATTTGGATT CTAGCATTTC     780
TACTTGCCTT CCCTCAGTGT CTTTATTCCA AAACCAAAGT CATGCCAGGC CGTACTCTCT     840
GCTTTGTGCA ATGGCCAGAA GGTCCCAAAC AACATTTCAC TTACCATATT ATCGTCATTA     900
TACTGGTGTA CTGTTTCCCA TTGCTCATCA TGGGTATTAC ATACACCATT                950
GTTGGAATTA CTCTCTGGGG AGGAGAAATC CCAGGAGATA CCTGTGACAA GTATCATGAG    1010
CAGCTAAAGG CCAAAAGAAA GGTTGTCAAA ATGATGATTA TTGTTGTCAT GACATTTGCT    1070
ATCTGCTGGC TGCCCTATCA TATTTACTTC ATTCTCACTG CAATCTATCA ACAACTAAAT    1130
AGATGGAAAT ACATCCAGCA GGTCTACCTG GCTAGCTTTT GGCTGGCAAT GAGCTCAACC    1190
ATGTACAATC CCATCATCTA CTGCTGTCTG AATAAAAGAT TCGAGCTGG CTTCAAGAGA     1250
GCATTTCGCT GGTGTCCTTT CATCAAAGTT TCCAGCTATG ATGAGCTAGA GCTCAAGACC    1310
ACCAGGTTTC ATCCAAACCG GCAAAGCAGT ATGTACACCG TGACCAGAAT GGAGTCCATG    1370
ACAGTCGTGT TTGACCCCAA CGATGCAGAC ACCACCAGGT CCAGTCGGAA GAAAAGAGCA    1430
ACGCCAAGAG ACCCAAGTTT CAATGGCTGC TCTCGCAGGA ATTCCAAATC TGCCTCCGCC    1490
ACTTCAAGTT TCATAAGCTC ACCCTATACC TCTGTGGATG AATATTCTTA ATTCCATTTC    1550
CTGAGGTAAA AGATTAGTGT GAGACCATCA TGGTGCCAGT CTAGGACCCC ATTCTCCTAT    1610
TTATCAGTCC TGTCCTATAT ACCCTCTAGA AACAGAAAGC AATTTTTAGG CAGCTATGGT    1670
CAAATTGAGA AAGGTAGTGT ATAAATGTGA CAAAGACACT AATAACATGT TAGCCTCCAC    1730
CCAAAATAAA ATGGGCTTTA AATTT                                          1755
``` or a degenerate variation thereof.

A third embodiment of this invention concerns systems for expressing all or part of the human neurokinin-3 receptor.

One class this third embodiment of the invention comprises:

A plasmid which comprises:
(a) a mammalian expression vector, such as pcDNAI/Neo, and
(b) a base sequence encoding human neurokinin-3 receptor protein.

Within this first class of the third embodiment the neurokinin-3 receptor comprises the nucleotide sequence (SEQ ID NO:2:) of complementary DNA as shown above.

A second class of this third embodiment of the invention concerns a system for the transient expression of human neurokinin-3 receptor in a monkey kidney cell line (COS), the system comprised of a vector which expresses human neurokinin receptor (human NK3R) cDNA.

Within this second class of the third embodiment is the sub-class wherein the expression system includes:
A plasmid which comprises:
(a) a mammalian expression vector, such as pcDNAI/Neo, and
(b) a base sequence encoding human neurokinin-3 receptor protein.

A third class of this third embodiment of the invention concerns a system for the expression of human neurokinin-3 receptor in a chinese hamster ovarian cell line (CHO), the system comprising a vector comprising human neurokinin-3 receptor (human NK3R) cDNA.

Within this third class of the third embodiment is the sub-class wherein the expression system includes:
A plasmid which comprises:
(a) a mammalian expression vector, such as pcNDAI/Neo and
(b) a base sequence encoding human neurokinin-3 receptor protein.

Within this sub-class the neurokinin-3 receptor expression system comprises the nucleotide sequence (SEQ ID NO:2:) of complementary DNA as shown above.

It is understood, and is readily apparent to those skilled in the art that a wide variety of commonly used cell lines are suitable for use in the present invention. Suitable cell lines derived from various species include, but are not limited to, cell lines of human, bovine, porcine, monkey, and rodent origin, or from yeast and bacterial strains.

A fourth embodiment of the invention concerns a method of using any of the above expression systems for determining the binding affinity of a test sample for human neurokinin-3 receptor.

In one class this fourth embodiment concerns a method of using a Chinese hamster ovarian cell line (CHO), the line transplanted with a plasmid,
which plasmid comprises:
(a) a mammalian expression vector, such as pcDNAI/Neo, and
(b) a base sequence encoding human neurokinin-3 receptor protein,
the method which comprises:
(1) expressing human neurokinin-3 receptor in the CHO cells;
(2) adding of a test sample to a solution containing $^{125}$I-eledoisin and the CHO cells;
(3) incubating the products of Step (2), the incubation being effective for competitive binding of the $^{125}$I-eledoisin and said test sample to the human neurokinin-3 receptor;
(4) separating the $^{125}$I-eledoisin which is bound to the human neurokinin-3 receptor from the $^{125}$I-eledoisin which is not bound;
(5) measuring the amount of the $^{125}$I-eledoisin which is bound to the human neurokinin-3 receptor.

In a second class this fourth embodiment concerns a method of using a monkey kidney cell line (COS), the line transplanted with a plasmid,.
which plasmid comprises:
(a) a mammalian expression vector, such as pcDNAI/Neo, and
(b) a base sequence encoding human neurokinin-3 receptor protein,
the method which comprises:
(1) expressing human neurokinin-3 receptor in the COS cells;
(2) adding of a test sample to a solution containing $^{125}$I-eledoisin and the COS cells;
(3) incubating the products of Step (2), the incubation being effective for competitive binding of the $^{125}$I-eledoisin and said test sample to the human neurokinin-3 receptor;
(4) separating the $^{125}$I-eledoisin which is bound to the human neurokinin-3 receptor from the $^{125}$I-eledoisin which is not bound;
(5) measuring the amount of the $^{125}$I-eledoisin which is bound to the human neurokinin-3 receptor.

In a third class this fourth embodiment concerns a method of using a Chinese hamster ovarian cell line (CHO), the line transplanted with a plasmid,
which plasmid comprises:
(a) a mammalian expression vector, such as pcDNAI/Neo, and
(b) the base sequence encoding human neurokinin-3 receptor protein,
the method which comprises:
(1) expressing human neurokinin-3 receptor in the CHO cells;
(2) equilibrating the product of Step (1) with $^3$H-myoinositol;
(3) washing the product of Step (2);
(4) incubating the product of Step (3) with a test sample and neurokinin-B in the presence of aqueous LiCl, resulting in the production of $^3$H-inositol monophosphate;
(5) measuring the $^3$H-inositol monophosphate.

In overview, the present invention describes methods to isolate the human neurokinin-3 receptor (human NK3R) complementary DNA (cDNA) without prior knowledge of its protein sequence or gene sequence. A polymerase chain reaction (PCR) technique was utilized for the isolation of human NK3R cDNA. In the approach, the regions of rat NK3R sequence thought to be similar to human NK3R were identified, oligonucleotide primers corresponding to those region were designed, PCR amplification was carried out to obtain a partial clone of the NK3R cDNA from human cells, and its DNA sequence was determined. The full length cDNA encoding the human NK3R was obtained from human mRNA utilizing the previous sequence information.

The complete sequence of the human NK3R cDNA was determined, and its encoded protein sequence was deduced. Among other things, such sequence information is useful in the process of developing novel neurokinin B antagonists.

Three heterologous expression systems were developed to express the cloned human NK3R cDNA. The Xenopus oocyte expression enables one to determine the biological function of human NK3R. The COS (a monkey kidney cell line) expression can be used to measure the ligand binding properties of human NK3R. The CHO (a Chinese hamster ovarian cell line) stable expression is suitable for natural product screen to identify potential therapeutic agents or other substances that bind to neurokinin-3 receptor or human NK3R. The cell line can also be used for determining the concentration of neurokinin B in human samples.

Assay protocols were developed to use the heterologously expressed human NK3R for the determination of the binding affinity and efficacy of neurokinin B agonists/antagonists with therapeutic potential.

The following examples are given for the purpose of illustrating the present invention and shall not be construed as being limitations on the scope or spirit of the instant invention.

EXAMPLE 1
Isolation of Human NK3R cDNA

To isolate the human NK3R cDNA in the absence of its sequence information, we developed methods to obtain three separate but overlapping cDNA clones in three steps. (i) We have adopted the homologous cloning strategy (Ohara et al., *Proc. Nat. Acad. Sci.*, 86:5673–5677 (1989)) to isolate cDNA clones encoding the central core region of human NK3R, with the assumption that the human NK3R sequence is similar to the published sequence (Shigemoto et al., *J. Biol. Chem.*, 265:623–628 (1990)) of rat NK3R in certain areas where appropriate PCR primers can be designed. Degenerate primers corresponding to the rat sequence were used in PCR amplification (Mullis and Faloona, *Meth. Enzymol.*, 155:335 (1987)) to obtain the cDNA encoding the central transmembrane core region of human NK3R from human mRNA. (ii) After determining the sequence of the core region in human NK3R, new primers corresponding to the human sequence were designed and anchored PCR amplification (Frohman, et al., *Proc. Nat. Acad. Sci.*, 85: 8998–9002 (1988)) was performed using the human primer in the core region. The cDNA encoding the N-terminal region of human NK3R was thus obtained from human mRNA and its sequence was determined. (iii) An anchored PCR strategy was also used to isolate the C-terminal region of human NK3R. To confirm the authenticity of the cDNA encoding human NK3R, an independent PCR amplification was performed to obtain the full length cDNA in a single step using primers from the 5' and 3' untranslated regions.

A cDNA clone encoding the central region of human NK3 receptor was obtained from human brain mRNA by PCR using degenerate primers based on the rat NK3 receptor sequence. The cDNA synthesis was initiated by the primer "ca" (SEQ ID NO:3:)

GGATCCTCRTCRTAGCTGGANAC using reverse transcriptase from BRL (Gaithersburg, Md.). Primary PCR was performed at 50° C. annealing temperature using the cDNA as template and primer "cb" (SEQ ID NO:4:)

TTTTGGATCCACTTGGATRAANGGRCA and primer "na" (SEQ ID NO:5:)

TTTTGGATCCTTCGTGCAGCCGTCCTGGCG

The following basic PCR conditions were used in all PCR experiments: 94° C. denaturation, 72° C. extension and 30 cycles. Secondary PCR was performed using the primary PCR product as template and the primer "cc" (SEQ ID NO:6:)

ATATGGATCCGACAGCAGCGAAATGCTCT and primer "nb" (SEQ ID NO:7:)

TTTTGAATTCTATGGCTTGGTGGTGGC under the same PCR conditions. A 900 bp cDNA fragment was obtained and sequenced, which was found to encode the central region of human NK3R.

A cDNA clone encoding the C-terminal region and 3' untranslated region of human NK3 receptor was obtained by anchored PCR using sense primers derived from the partial clone described above. The cDNA synthesis was initiated by the oligo-dT primer "notldt" (SEQ ID NO:8:)

TTTTGCGGCCGCTTTTTTTTTTTTTTTTT

It was followed by a tailing reaction using terminal deoxynucleotide transferase (Promega, Madison, Wis.) to add a poly(A) tail to the 3' end of the cDNA. Primary PCR was carried out using the cDNA as template and the primers "notldt" and "s1068" (SEQ ID NO:9:)

AATTGGATCCTAGATGGAAATACATCCAGC at 55° C. annealing temperature. Secondary PCR was carried out using the primary PCR product as template and the primers "notldt" and "s1106" (SEQ ID NO:10:)

AATTGGATCCTTGGCTGGCAATGAGCTCA under the same conditions. Tertiary PCR was carried out using the secondary PCR product as template and the primers "notldt" and "s1137" (SEQ ID NO:11:)

AATTGGATCCTCCCATCATCTACTGCTGTC under the same conditions. A 600 bp cDNA fragment was obtained and sequenced, which encodes the C-terminal region of human NK3R and 3' untranslated region.

A cDNA clone encoding the N-terminal region and 5' untranslated region of human NK3 receptor was obtained by anchored PCR using antisense primers derived from the partial clone encoding the central region of human NK3R. The cDNA synthesis was initiated using the primers "a475" (SEQ ID NO:12:)

TGGCGAACACAGCTGTGATA and "a400" (SEQ ID NO:13:)

AGCGCGTAGATGAAATTGAC

A poly(A) tail was then added to the 3' end of the cDNA. Primary PCR was performed using the cDNA as template and the primers "notldt" and "a351" (SEQ ID NO:14:)

AATTGCGGCCGCCGGAGAAAGCCAGGTTCACA at 60° C. annealing temperature. Secondary PCR was performed using the primary PCR product as template and the primers "notldt" and "a332" (SEQ ID NO:15:)

AATTGCGGCCGCAGGAAGTAGTTGGTGACAGTC under the same conditions. A 600 bp cDNA fragment was obtained and sequenced, which encodes the N-terminal region of human NK3R and 5' untranslated region.

To confirm the authenticity of the human NK3R cDNA sequence, an independent PCR was carried out to obtain the full length cDNA using primers based on the 5' and 3' untranslated regions. The cDNA was initiated using the primers "c1" (SEQ ID NO:16:)

AATTGCGGCCGCGACAGGACTGATAAATAGGAG and "c2" (SEQ ID NO:17:)

AATTGCGGCCGCCATGATGGTCTCACACTAATC

Primary PCR was performed using the cDNA as template and using the primers "c2" and "s50" (SEQ ID NO:18:)

AAAGTGACCAGGAGGCAGAGA at 60° C. annealing temperature. Secondary PCR was performed using the primary PCR product as template and the primers "c3" (SEQ ID NO:19:)

AATTGCGGCCGCACCTCAGGAAATGGAATTAAG and "s71" (SEQ ID NO:20:)

AATTGGATCCAGAACTTCAGAGGAGTCTCG under the same conditions. A 1500 bp cDNA fragment was obtained and its sequence was consistent with the previous partial clones.

EXAMPLE 2
Expression of the Cloned Human NK3R

Three expression systems were developed for the cloned human NK3R. An transient expression in Xenopus oocytes resulted from microinjection of in vitro transcribed mRNA from the cloned cDNA (Xenopus Laevis from XENOPUS ONE, Ann Arbor, Mich.). This system allows the measurement of biological effect of NK3R activation upon ligand binding. Another transient expression in COS (a monkey kidney cell line, ATCC CRL 1651, ATCC Manassas, Va.) resulted from the transfection of the cloned cDNA under the control of viral promoter into mammalian cells (e.g., COS). The transfected cells are suitable for determination of the binding affinity of human NK3R for various ligands. Stable expression of human NK3R in mammalian cells (e.g., CHO, a Chinese hamster ovarian cell line, ATCC CRL 9096, ATCC Manassas, VA) was achieved after integration of the transfected cDNA into the chromosomes of the host cells. These stable cell lines will constituently express the cloned human NK3R and can be propagated infinitely. Therefore, a stable expression system is very useful in large scale drug screening, and can be used to determine the concentration of neurokinin-B related substances in biopsy samples of patients.

To express the cloned human NK3R, the full length cDNA of human NK3 receptor was subcloned into the expression vector pcDNA-Neo (Invitrogen, San Diego, Calif.). Transient expression in COS cells was achieved by electroporation using the IBI GeneZapper (IBI, New Haven, Conn.). The transfected cells were incubated in 10% fetal calf serum, 100 U/ml penicillin-streptomycin, and 90% DMEM media (Gibco, Grand Island, N.Y.) in a 5% $CO_2$ incubator at 37° C. for three days before the binding assay.

To establish a stable cell line expressing the cloned human NK3R, the cDNA in the expression vector pcDNA-Neo was transfected into CHO cells by electroporation. The transfected cells were incubated in the selection media (10% fetal calf serum, 100 U/ml penicillin-streptomycin, 1/500 hypoxanthine-thymidine, 90% IMDM media (JRH Biosciences, Lenexa, Kans.), 0.7 mg/ml neomycin) in a 5% $CO_2$ incubator until colonies were visible. Each colony was separated and propagated to maintain stable cell lines.

Both the COS expression and CHO expression allow the determination of binding affinity of various agonists and antagonists at the human NK3R.

The cloned human NK3R was expressed in Xenopus oocytes to demonstrate the biological function of human NK3 receptor as an activator of the second messenger inositol trisphosphate. The in vitro mRNA transcript was synthesized from the cDNA in pcDNA-Neo using T7 RNA polymerase (Stratagene, San Diego, Calif.) and injected into Xenopus oocytes. The oocytes were incubated at 19° C. for two days before electrophysiological assay.

EXAMPLE 3
Assays

The binding assay of human NK3R expressed in COS cells or CHO cells is based on the use of $^{125}$I-Bolton Hunter labeled eledoisin ($^{125}$I-BHE, from Du Pont, Boston, Mass.) (or $^{125}$I-NKB) as a radioactively labeled ligand which compete with unlabeled neurokinin peptides or any other ligand for binding to the human NK3R. Monolayer cell culture of COS or CHO was dissociated by the non-enzymatic solution (Specialty Media, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 0.2 ml of the cell suspension would give rise to about 10,000 cpm of specific $^{125}$I-BHE binding (approximately 50,000 to 200,000 cells). In the binding assay, 0.2 ml of cells were added to a tube containing 0.02 ml of 2.5 nM of $^{125}$I-BHE and 0.02 ml of unlabeled test compound. The tubes were incubated at 4° C. for 1 hour with gentle shaking. The bound radioactivity was separated from unbound radioactivity by GF/C filter (Brandel, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The electrophysiological assay of human NK3R expressed in Xenopus oocytes was based on the fact that NK3R activates the phospholipase C upon agonist binding, and phospholipase C in turn increases the intracellular calcium concentration through inositol trisphosphate ($IP_3$) and $IP_3$-gated calcium channel on intracellular membranes. The calcium increase activates calcium-gated chloride channels on plasma membranes which gives rise to a chloride current measurable by two electrode voltage clamp.

The oocyte was voltage-clamped at −80 mV by the model 8500 intracellular preamp-clamp (Dagan, Minneapolis, Minn.). The recoding chamber was continuously perfused with recording buffer (96 mM NaCl, 2 mM KC1, 1.8 mM $CaCl_2$, 5 mM HEPES, pH 7.4). Chloride current was elicited by applying agonist (from 0.1 nM to 1000 nM) to the recording chamber. At least three oocytes were measured for each concentration. The antagonistic activity of any potential NK3 antagonist can be assessed by determining the inhibition of neurokinin B response. Likewise, NK3 agonists can be identified by their ability to stimulate a response in oocytes injected with NK3R mRNA but not in uninjected oocytes.

The activation of phospholipase C by the human NK3R may also be measured in CHO cells by determining the accumulation of inositol monophosphate which is a degradation product of $IP_3$. CHO cells are seeded in 12-well plate at 250,000 cells per well. After incubating in CHO media for 4 days, cells are loaded with 0.025 mCi/ml of $^3$H-myoinositol by overnight incubation. The extracellular radioactivity is removed by washing with phosphate buffered saline. LiCl is added to the well at final concentration of 0.1 mM with or without antagonist, and continued incubation at 37° C. for 15 min. Neurokinin B is added to the well at final concentration of 0.3 nM to activate the human NK3R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter.

In addition to large scale drug screening using the stable CHO cell line expressing the cloned human NK3R, other alternative applications are obvious. For example, the stable cell line can be used in an assay to determine the neurokinin B concentration in human samples.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A method for determining the binding of a test sample to the human neurokinin-3 receptor using a Chinese hamster ovarian cell line (CHO), the cell line transplanted with a plasmid, which plasmid comprises:
(a) a mammalian expression vector, and
(b) a sequence of nucleotides encoding the human neurokinin-3 receptor protein, wherein the sequence comprises a sequence of nucleotides a shown in SEQ ID NO:2:, the method which comprises:

(1) expressing human neurokinin-3 receptor in the CHO cells;
(2) adding a test sample to a solution containing $^{125}$I-eledoisin and the CHO cells;
(3) incubating the products of Step 2, wherein the incubation is effective for competitive binding of the $^{125}$I-eledoisin and the test sample to the human neurokinin receptor;

(4) separating the $^{125}$I-eledoisin which is bound to the human neurokinin receptor from the $^{125}$I-eledoisin which is not bound;

(5) measuring the amount of the $^{125}$I-eledoisin which is bound to the human neurokinin-3 receptor; and (6) comparing the amount of the $^{125}$I-eledoisin which is bound to the human neurokinin-3 receptor to the amount of $^{125}$I-eledoisin which is not bound to determine the binding of the test sample to the human neurokinin-3 receptor.

2. The method of claim 1 wherein the mammalian expression vector is pcDNAI/Neo.

3. A method for determining the binding of a test sample to the human neurokinin-3 receptor using a monkey kidney cell line (COS), the cell line transplanted with a plasmid, which plasmid comprises:

(a) a mammalian expression vector, and (b) a sequence of nucleotides encoding the human neurokinin-3 receptor protein, wherein the sequence comprises a sequence of nucleotides a shown in SEQ ID NO:2:, the method which comprises:

(1) expressing human neurokinin-3 receptor in the CHO cells;

(2) adding a test sample to a solution containing $^{125}$I-eledoisin and the CHO cells;

(3) incubating the products of Step 2, wherein the incubation is effective for competitive binding of the $^{125}$I-eledoisin and the test sample to the human neurokinin receptor;

(4) separating the $^{125}$I-eledoisin which is bound to the human neurokinin receptor from the $^{125}$I-eledoisin which is not bound;

(5) measuring the amount of the $^{125}$I-eledoisin which is bound to the human neurokinin-3 receptor; and (6) comparing the amount of the $^{125}$I-eledoisin which is bound to the human neurokinin-3 receptor to the amount of $^{125}$I-eledoisin which is not bound to determine the binding of the test sample to the human neurokinin-3 receptor.

4. The method of claim 3 wherein the mammalian expression vector is pcDNAI/Neo.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 465 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

```
Met Ala Thr Leu Pro Ala Ala Glu Thr Trp Ile Asp Gly Gly Gly
1               5                   10                  15

Val Gly Ala Asp Ala Val Asn Leu Thr Ala Ser Leu Ala Ala Gly Ala
            20                  25                  30

Ala Thr Gly Ala Val Glu Thr Gly Trp Leu Gln Leu Leu Asp Gln Ala
            35                  40                  45

Gly Asn Leu Ser Ser Ser Pro Ser Ala Leu Gly Leu Pro Val Ala Ser
        50                  55                  60

Pro Ala Pro Ser Gln Pro Trp Ala Asn Leu Thr Asn Gln Phe Val Gln
65                  70                  75                  80

Pro Ser Trp Arg Ile Ala Leu Trp Ser Leu Ala Tyr Gly Val Val Val
                85                  90                  95

Ala Val Ala Val Leu Gly Asn Leu Ile Val Ile Trp Ile Ile Leu Ala
                100                 105                 110

His Lys Arg Met Arg Thr Val Thr Asn Tyr Phe Leu Val Asn Leu Ala
            115                 120                 125

Phe Ser Asp Ala Ser Met Ala Ala Phe Asn Thr Leu Val Asn Phe Ile
        130                 135                 140

Tyr Ala Leu His Ser Glu Trp Tyr Phe Gly Ala Asn Tyr Cys Arg Phe
145                 150                 155                 160

Gln Asn Phe Phe Pro Ile Thr Ala Val Phe Ala Ser Ile Tyr Ser Met
                165                 170                 175

Thr Ala Ile Ala Val Asp Arg Tyr Met Ala Ile Ile Asp Pro Leu Lys
            180                 185                 190

Pro Arg Leu Ser Ala Thr Ala Thr Lys Ile Val Ile Gly Ser Ile Trp
        195                 200                 205

Ile Leu Ala Phe Leu Leu Ala Phe Pro Gln Cys Leu Tyr Ser Lys Thr
        210                 215                 220

Lys Val Met Pro Gly Arg Thr Leu Cys Phe Val Gln Trp Pro Glu Gly
225                 230                 235                 240

Pro Lys Gln His Phe Thr Tyr His Ile Ile Val Ile Ile Leu Val Tyr
                245                 250                 255

Cys Phe Pro Leu Leu Ile Met Gly Ile Thr Tyr Thr Ile Val Gly Ile
            260                 265                 270

Thr Leu Trp Gly Gly Glu Ile Pro Gly Asp Thr Cys Asp Lys Tyr His
        275                 280                 285

Glu Gln Leu Lys Ala Lys Arg Lys Val Val Lys Met Met Ile Ile Val
        290                 295                 300

Val Met Thr Phe Ala Ile Cys Trp Leu Pro Tyr His Ile Tyr Phe Ile
305                 310                 315                 320
```

```
Leu Thr Ala Ile Tyr Gln Gln Leu Asn Arg Trp Lys Tyr Ile Gln Gln
                325                 330                 335
Val Tyr Leu Ala Ser Phe Trp Leu Ala Met Ser Ser Thr Met Tyr Asn
                340                 345                 350
Pro Ile Ile Tyr Cys Cys Leu Asn Lys Arg Phe Arg Ala Gly Phe Lys
                355                 360                 365
Arg Ala Phe Arg Trp Cys Pro Phe Ile Lys Val Ser Ser Tyr Asp Glu
                370                 375                 380
Leu Glu Leu Lys Thr Thr Arg Phe His Pro Asn Arg Gln Ser Ser Met
385                 390                 395                 400
Tyr Thr Val Thr Arg Met Glu Ser Met Thr Val Val Phe Asp Pro Asn
                405                 410                 415
Asp Ala Asp Thr Thr Arg Ser Ser Arg Lys Lys Arg Ala Thr Pro Arg
                420                 425                 430
Asp Pro Ser Phe Asn Gly Cys Ser Arg Arg Asn Ser Lys Ser Ala Ser
                435                 440                 445
Ala Thr Ser Ser Phe Ile Ser Ser Pro Tyr Thr Ser Val Asp Glu Tyr
                450                 455                 460
Ser
465

(2) INFORMATION FOR SEQ ID NO:2:

(i) SEQUENCE CHARACTERISTICS:
        (A) LENGTH: 1755 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

CTATTGCAGT ATCTTTCAGC TTCCAGTCTT ATCTGAAGAC CCCGGCACCA AAGTGACCAG      60

GAGGCAGAGA AGAACTTCAG AGGAGTCTCG TCTTGGGCTG CCCGTGGGTG AGTGGGAGGG     120

TCCGGGACTG CAGACCGGTG GCGATGGCCA CTCTCCCAGC AGCAGAAACC TGGATAGACG     180

GGGGTGGAGG CGTGGGTGCA GACGCCGTGA ACCTGACCGC CTCGCTAGCT GCCGGGGCGG     240

CCACGGGGGC AGTTGAGACT GGGTGGCTGC AACTGCTGGA CCAAGCTGGC AACCTCTCCT     300

CCTCCCCTTC CGCGCTGGGA CTGCCTGTGG CTTCCCCCGC GCCCTCCCAG CCCTGGGCCA     360

ACCTCACCAA CCAGTTCGTG CAGCCGTCCT GGCGCATCGC GCTCTGGTCC CTGGCGTATG     420

GTGTGGTGGT GGCAGTGGCA GTTTTGGGAA ATCTCATCGT CATCTGGATC ATCCTGGCCC     480

ACAAGCGCAT GAGGACTGTC ACCAACTACT TCCTTGTGAA CCTGGCTTTC TCCGACGCCT     540

CCATGGCCGC CTTCAACACG TTGGTCAATT TCATCTACGC GCTTCATAGC GAGTGGTACT     600

TTGGCGCCAA CTACTGCCGC TTCCAGAACT TCTTTCCTAT CACAGCTGTG TTCGCCAGCA     660

TCTACTCCAT GACGGCCATT GCGGTGGACA GGTATATGGC TATTATTGAT CCCTTGAAAC     720

CCAGACTGTC TGCTACAGCA ACCAAGATTG TCATTGGAAG TATTTGGATT CTAGCATTTC     780

TACTTGCCTT CCCTCAGTGT CTTTATTCCA AAACCAAAGT CATGCCAGGC CGTACTCTCT     840

GCTTTGTGCA ATGGCCAGAA GGTCCCAAAC AACATTTCAC TTACCATATT ATCGTCATTA     900

TACTGGTGTA CTGTTTCCCA TTGCTCATCA TGGGTATTAC ATACACCATT                 950

GTTGGAATTA CTCTCTGGGG AGGAGAAATC CCAGGAGATA CCTGTGACAA GTATCATGAG    1010

CAGCTAAAGG CCAAAAGAAA GGTTGTCAAA ATGATGATTA TTGTTGTCAT GACATTTGCT    1070
```

```
ATCTGCTGGC TGCCCTATCA TATTTACTTC ATTCTCACTG CAATCTATCA ACAACTAAAT    1130

AGATGGAAAT ACATCCAGCA GGTCTACCTG GCTAGCTTTT GGCTGGCAAT GAGCTCAACC    1190

ATGTACAATC CCATCATCTA CTGCTGTCTG AATAAAAGAT TTCGAGCTGG CTTCAAGAGA    1250

GCATTTCGCT GGTGTCCTTT CATCAAAGTT TCCAGCTATG ATGAGCTAGA GCTCAAGACC    1310

ACCAGGTTTC ATCCAAACCG GCAAAGCAGT ATGTACACCG TGACCAGAAT GGAGTCCATG    1370

ACAGTCGTGT TTGACCCCAA CGATGCAGAC ACCACCAGGT CCAGTCGGAA GAAAAGAGCA    1430

ACGCCAAGAG ACCCAAGTTT CAATGGCTGC TCTCGCAGGA ATTCCAAATC TGCCTCCGCC    1490

ACTTCAAGTT TCATAAGCTC ACCCTATACC TCTGTGGATG AATATTCTTA ATTCCATTTC    1550

CTGAGGTAAA AGATTAGTGT GAGACCATCA TGGTGCCAGT CTAGGACCCC ATTCTCCTAT    1610

TTATCAGTCC TGTCCTATAT ACCCTCTAGA AACAGAAAGC AATTTTTAGG CAGCTATGGT    1670

CAAATTGAGA AAGGTAGTGT ATAAATGTGA CAAAGACACT AATAACATGT TAGCCTCCAC    1730

CCAAAATAAA ATGGGCTTTA AATTT                                          1755
```

(2) INFORMATION FOR SEQ ID NO:3:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:3:

```
GGATCCTCRT CRTAGCTGGA NAC                                              23
```

(2) INFORMATION FOR SEQ ID NO:4:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:4:

```
TTTTGGATCC ACTTGGATRA ANGGRCA                                          27
```

(2) INFORMATION FOR SEQ ID NO:5:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:5:

```
TTTTGGATCC TTCGTGCAGC CGTCCTGGCG                                       30
```

(2) INFORMATION FOR SEQ ID NO:6:

(i) SEQUENCE CHARACTERISTICS:
  (A) LENGTH: 29 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:6:

ATATGGATCC GACAGCAGCG AAATGCTCT                                29

(2) INFORMATION FOR SEQ ID NO:7:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:7:

TTTTGAATTC TATGGCTTGG TGGTGGC                                  27

(2) INFORMATION FOR SEQ ID NO:8:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:8:

TTTTGCGGCC GCTTTTTTTT TTTTTTTTT                                29

(2) INFORMATION FOR SEQ ID NO:9:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:9:

AATTGGATCC TAGATGGAAA TACATCCAGC                               30

(2) INFORMATION FOR SEQ ID NO:10:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:10:

AATTGGATCC TTGGCTGGCA ATGAGCTCA                                29

(2) INFORMATION FOR SEQ ID NO:11:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:11:

AATTGGATCC TCCCATCATC TACTGCTGTC                                  30

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

TGGCGAACAC AGCTGTGATA                                             20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

AGCGCGTAGA TGAAATTGAC                                             20

(2) INFORMATION FOR SEQ ID NO:14:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

AATTGCGGCC GCCGGAGAAA GCCAGGTTCA CA                               32

(2) INFORMATION FOR SEQ ID NO:15:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

AATTGCGGCC GCAGGAAGTA GTTGGTGACA GTC                              33

(2) INFORMATION FOR SEQ ID NO:16:

(i) SEQUENCE CHARACTERISTICS:
            (A) LENGTH: 33 base pairs
            (B) TYPE: nucleic acid
            (C) STRANDEDNESS: single
            (D) TOPOLOGY: linear -continued (ii) MOLECULE TYPE: cDNA (xi) SEQUENCE DESCRIPTION: SEQ ID NO:16:

AATTGCGGCC GCGACAGGAC TGATAAATAG GAG                33

(2) INFORMATION FOR SEQ ID NO:17:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:17:

AATTGCGGCC GCCATGATGG TCTCACACTA ATC                33

(2) INFORMATION FOR SEQ ID NO:18:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:18:

AAAGTGACCA GGAGGCAGAG A                             21

(2) INFORMATION FOR SEQ ID NO:19:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:19:

AATTGCGGCC GCACCTCAGG AAATGGAATT AAG                33

(2) INFORMATION FOR SEQ ID NO:20:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:20:

AATTGGATCC AGAACTTCAG AGGAGTCTCG                    30